(12) United States Patent
Vizethum et al.

(10) Patent No.: US 9,034,622 B2
(45) Date of Patent: May 19, 2015

(54) PREPARATION FOR PHOTODYNAMIC CONTROL OF MICROORGANISMS AND USE THEREOF

(75) Inventors: Freimut Vizethum, Mannheim (DE); Reinhold Schuetze, Attnang-Puchheim (AT)

(73) Assignee: bredent medical GmbH & Co. KG, Senden (DE)

( * ) Notice: Subject to any disclaimer, the term of this patent is extended or adjusted under 35 U.S.C. 154(b) by 36 days.

(21) Appl. No.: 12/839,846

(22) Filed: Jul. 20, 2010

(65) Prior Publication Data

US 2010/0291654 A1 Nov. 18, 2010

Related U.S. Application Data

(63) Continuation of application No. 11/578,751, filed as application No. PCT/EP2005/004032 on Apr. 15, 2005, now abandoned.

(30) Foreign Application Priority Data

Apr. 16, 2004 (DE) .......................... 10 2004 019 247
May 27, 2004 (WO) .................. PCT/EP2004/005719

(51) Int. Cl.
*A61K 41/00* (2006.01)
*A61K 31/5415* (2006.01)
*A61N 5/06* (2006.01)
*A61Q 11/00* (2006.01)
*A61L 2/08* (2006.01)

(52) U.S. Cl.
CPC ......... *A61K 41/0057* (2013.01); *A61K 31/5415* (2013.01); *A61N 5/062* (2013.01); *A61Q 11/00* (2013.01); *A61L 2/088* (2013.01)

(58) Field of Classification Search
None
See application file for complete search history.

(56) References Cited

U.S. PATENT DOCUMENTS

| | | | | |
|---|---|---|---|---|
| 4,052,536 A | * | 10/1977 | Lichtin et al. | 429/105 |
| 4,146,712 A | * | 3/1979 | Loew | 544/135 |
| 4,975,419 A | * | 12/1990 | Newton et al. | 514/9.4 |
| 5,413,924 A | * | 5/1995 | Kosak et al. | 435/177 |
| 5,597,722 A | * | 1/1997 | Chapman et al. | 435/238 |
| 5,614,502 A | * | 3/1997 | Flotte et al. | 514/34 |
| 5,955,256 A | * | 9/1999 | Sowemimo-Coker et al. | 435/2 |
| 6,294,361 B1 | * | 9/2001 | Horowitz et al. | 435/173.3 |
| 2002/0183808 A1 | * | 12/2002 | Biel | 607/88 |
| 2002/0197649 A1 | * | 12/2002 | Singh | 435/7.1 |
| 2004/0052798 A1 | * | 3/2004 | Neuberger | 424/184.1 |

FOREIGN PATENT DOCUMENTS

| | | |
|---|---|---|
| WO | WO-93/21992 | 11/1993 |
| WO | WO-94/28120 | 12/1994 |
| WO | WO-96/36704 | 11/1996 |
| WO | WO 0062701 A2 * | 10/2000 |
| WO | WO-01/87416 | 11/2001 |
| WO | WO-02/096471 | 12/2002 |
| WO | WO-03/066109 | 8/2003 |

OTHER PUBLICATIONS

Moore, DD. 1996. Commonly used reagents and equipment. Curr. Protoc. Mol. Biol. Supplement 35. A.2.3.*
Komerik, N. et al. In vivo killing of *Porphyromonas gingivalis* by toluidine blue-mediated photosensitization in an animal model. Antimicrobial Agents and Chemotherapy. Mar. 2003. 47(3): 932-940.*
Bhatti, M et al. A study of the uptake of toluidine blue O by *Porphyromonas gingivalis* and the mechanism of lethal photosensitization. Photochemistry and Photobiology. 1998. 68(3): 370-376.*
Shimon Gross, et al.: "Protein-A-mediated Targeting of Bacteriochlorophyll-IgG to *Staphylococcus aureus*: A Model for Enhanced Site-Specific Photocytotoxicity", Photochemistry and Photobiology, 1997, 66(6): pp. 872-878.
M.C. Teichert, et al.: "Treatment of oral candidiasis with methylene blue-mediated photodynamic therapy in an immunodeficient murine model", Oral Surgery Oral Medicine Opal Pathology, Feb. 2002, pp. 155-160.

\* cited by examiner

*Primary Examiner* — Allison Fox
*Assistant Examiner* — Susan E Fernandez
(74) *Attorney, Agent, or Firm* — Jordan and Hamburg LLP

(57) ABSTRACT

The invention relates to a preparation for the photodynamic control of micro-organisms, said preparation being in a liquid or pasty form and containing a photosensitizer which comprises a dyestuff and produces singlet oxygen when irradiated by means of light. The micro-organisms can be marked by means of the dyestuff. The aim of the invention is to improve said preparation in order to enable an improved photodynamic control. To this end, the preparation contains an active ingredient for amplifying or weakening the oxidative action of the singulet oxygen by chemical manipulation of the dyestuff or the nanoenvironment thereof. In a particular form of embodiment, a rinsing solution is used before the irradiation.

21 Claims, No Drawings

PREPARATION FOR PHOTODYNAMIC CONTROL OF MICROORGANISMS AND USE THEREOF

REFERENCE TO RELATED APPLICATION

This is a continuation application of Ser. No. 11/578,751, filed Nov. 29, 2006 which is currently pending. The subject matter of the aforementioned prior application is hereby incorporated herein by reference.

The invention relates to a preparation for photodynamic control of microorganisms in accordance with the features listed in patent claim 1. The invention furthermore relates to the use of such a preparation.

Known from WO 01/87416 A1 is an arrangement and method for reducing or destroying microorganisms such as bacteria using a light-activatable substance, known from photodynamic therapy (PDT). Using the light-activatable substance, in particular a dye, the microorganisms are sensitized and/or stained, and, after irradiation with light having a suitable wavelength and energy density, are killed. After the selective effect and/or staining of the microorganisms, the principle of action of PDT is based on the physical action of the transfer of energy to the light-activatable substance, which is also called the photosensitizer. From there, the energy for reactions can be made available to the cell membrane. The energy produced by means of an irradiation device, in particular a laser device, is thus concentrated on the microorganisms and the equilibrium of reactions that also occur in the non-irradiated condition in the "normal" environment are [sic] displaced and consequently the microorganisms are destroyed.

Moreover, known from EP 0 637 976 B1 is the use of a light-sensitizing substance or compound or photosensitizer (PS) in the production of a medication for use during disinfection or sterilization of tissue in the oral cavity or of a wound or lesion in the oral cavity by destroying microbes that are associated with a disease and that are in a periodontal pocket in the region between the tooth and the gum. In this case, the photosensitizer is applied to the tissue, wound, or lesion, the microbes associated with a disease absorbing the photosensitizer. The tissue, wound, or lesion is irradiated with laser light at a wavelength that the photosensitizer absorbs. The reduction in microbes for this combined stain and laser treatment is described for various microbes and photosensitizers in the form of solutions that include, among other things, methylene blue and toluidine blue in different, quite small concentrations, specifically from 0.01 to 0.00125% (weight per volume), the effect of the applied energy density also being covered. HeNe lasers with a wavelength of 634 nm and an output of 7.3 mW as well as GaAs lasers with a wavelength of 660 nm and an output of 11 mW are used for light sources.

Photodynamic therapy is a photochemical method that in the past was used primarily in cancer treatment. The term "photodynamic therapy" in general is understood to be light-induced inactivation of cells, microorganisms, and molecules.

A modification to this principle is being used today to control microorganisms—"antimicrobial photodynamic therapy" (APT). The goal is not to destroy endogenous (tumor) cells, but rather the deliberate control of local infections, the control of microorganisms. The principle of action of APT is based on the selective staining of microorganisms in the biofilm using a so-called photosensitizer and the destruction of the microorganisms using irradiation with a suitable laser matched to the photosensitizer.

Substances that can be used for photosensitizers, for instance thiazine dyes, are able to absorb light of a suitable wavelength and thereby convert to the excited so-called triplet state.

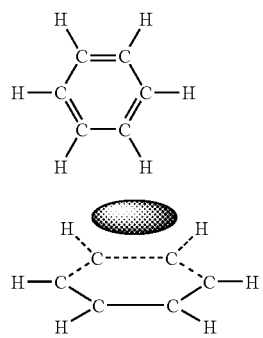

Aromatic Carbon Rings as Basic Components of Chromophore Molecules

Systemically applicable photosensitizers are used primarily in cancer therapies. These are directed against endogenous cells, are administered systemically according to certain pharmacological principles in order to enrich tumors with them and then to activate them using irradiation with light. This application is distinguished in principle from that for controlling superficial infections.

A number of requirements must be satisfied for a substance to be able to be employed as an effective photosensitizer for this clinical application. The active substance should:
1. Be non-toxic
2. Possess suitable penetration properties and high bacterial affinity
3. Have suitable spectral properties
4. Be simple and safe to apply
5. Effect complete coverage of the therapy area
6. Possess suitable viscosity, greatest possible thixotropic properties
7. Also be able to be used on open wounds
8. Be as painless as possible to use
9. Attain high triplet quantum yield (high singlet oxygen production)
10. Be stable over time
11. Be approved according to the pharmaceutical or medical product law Photosensitizers can absorb light (energy) into their structure and them make it available again for further reactions as chemical energy. A special excited and very reactive form of oxygen is then formed from the oxygen molecules that are present in the environment of the excited photosensitizer molecules—so-called singlet oxygen.

The following reactions, in principle and simplified, occur:

|  | Initial product | → | Reaction product | Lifetime (sec) |
|---|---|---|---|---|
| Equation 1: | $^1\text{Sensitizer} + \text{light} (h*v)$ | → | $^3\text{Sensitizer}^{excited}$ | $10^{-9}$ |
| Equation 2: | $^3\text{Sensitizer}^{excited}$ |  | $^3\text{Sensitizer}^{metastable}$ | $>10^{-6}$ |
| Equation 3: | $^3\text{Sensitizer}^{metastable} + {}^3O_2$ |  | $^1\text{Sensitizer} + {}^1O_2$ | $10^{-6}\text{-}10^{-3}$ |

Under the influence of appropriate light and oxygen, the photosensitizing substances react according to given reaction paths. The photons h radiated in during the antimicrobial photodynamic therapy excite the photosensitizer coupled to the microorganisms ($^1$Sens) due to its high absorbability (Equation 1). Within nanoseconds the excited sensitizer molecule converts to a metastable triplet condition with a longer lifetime, in accordance with Equation (2). The time in the triplet condition (in the range of microseconds) is relatively long compared to other excitation conditions (in the picosecond and nanosecond range) and therefore is ideal as a starting point for photochemical reactions such as e.g. transferring the excitation energy to an oxygen molecule. The excited oxygen assumes the energetically higher singlet condition with a relatively longer lifetime (Equation 3).

The basic principle of the antimicrobial photodynamic effect is thus based on the local formation of singlet oxygen and consequently of reactive radicals. This activated singlet oxygen initiates oxidation of molecules primarily in the cell wall of the microorganisms and thus initiates cytolysis. Once the supply of energy is turned off, the process comes to a halt very rapidly, in fractions of a second, due to the very short lifetime of the activated molecules. Now the photosensitizer is not consumed with the energy doses applied if these are in the range of 3 J/cm2 to 6 J/cm2, because in this so-called photobleaching—the destruction of the photosensitizer molecule by light—cannot be detected but rather remains in or on the tissue. Thus for instance treated areas exposed to sunlight can continue to react in an undesired manner and cause secondary effects.

Proceeding from this point the underlying object of the invention is to further develop the preparation such that improved control of microorganisms is attained.

This object is attained in accordance with the features provided in patent claim 1.

By means of the inventively suggested preparation, which in a liquid or paste form stains bacteria with a dye, in conjunction with the activation or deactivation of this dye in terms of its light absorption, intensification or weakening of the oxidative effect of occurring singlet oxygen is attained using chemical manipulation of the dye or its nanoenvironment.

In accordance with the invention it is assumed that photosensitizers such as for instance phenothiazine dyes, without this being a limitation, can react in various structurally similar forms depending on the nanoenvironment, as can be seen in the following for methylene blue:

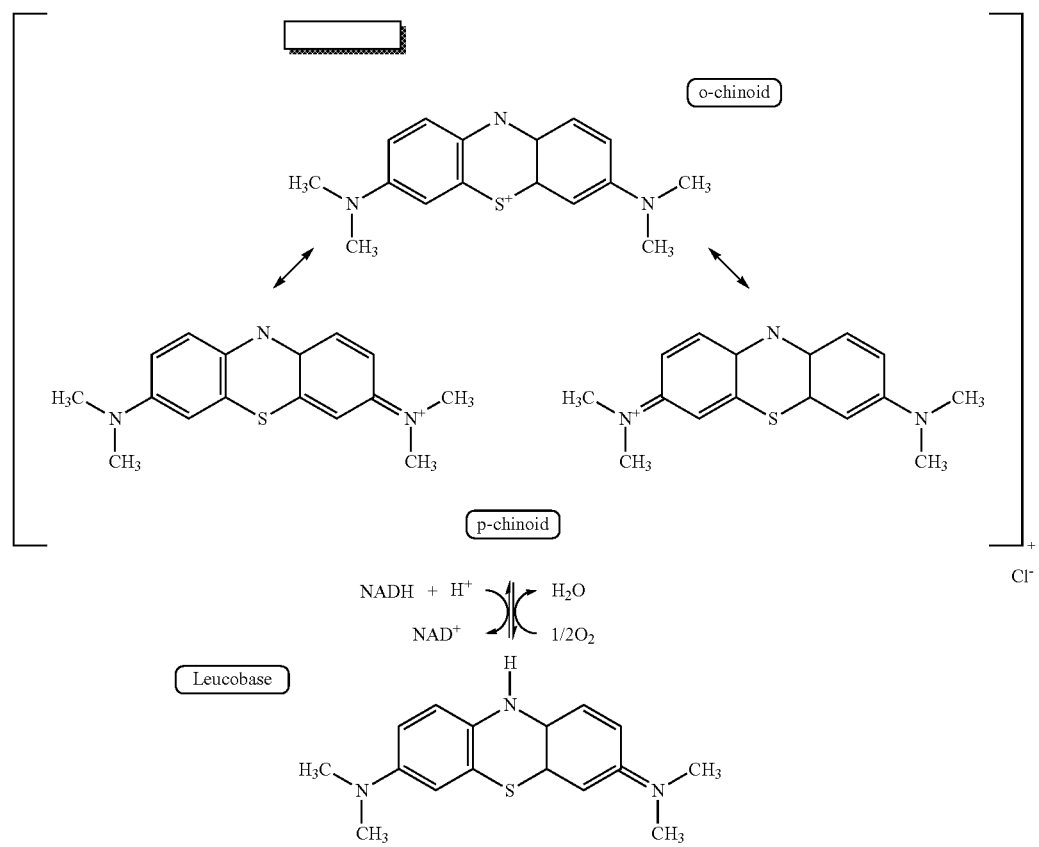

The leucoform of the methylene blue is for instance not photoactive and is colorless, while the o- and p-chinoid forms are suitable photosensitizers.

Using deliberate change to the nanoenvironment of the molecules, it is thus possible to intentionally turn the effect on and off in that the absorbed photosensitizer molecules can be turned on or off by protonation using chemical proton donors.

The inventive preparation contains dyes that can be reversibly converted from the active form to the inactive form, and vice versa, using simple chemical reactions. After the therapy they are present in the body as harmless molecules and can be broken down and excreted. On the other hand, those that are still present possibly after a period x (x=hours or days) can be re-"activated" by deliberately changing the nanoenvironment.

Potential "switching" substances that are particularly suitable for "switching" and their general importance in metabolism as reducing agents shall be explained in the following, without this resulting in a limitation.

1. Glutathione

Glutathione in reduced (GSH) and oxidized (GSSG) forms have the following structures:

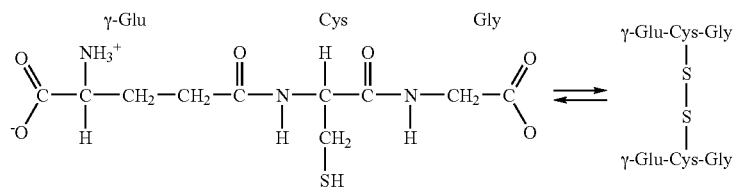

Glutathione is an amino acid derivative that plays a different important role in the metabolism of cells and that is present in a high concentration. Glutathione is included in a redox cycle in that it occurs in oxidized form (GSSG) and in reduced form (GSH). Oxidized glutathione comprises two tripeptides chained to one another by a disulfide compound, while the reduced thiol form represents a single tripeptide with one free sulfhydryl group. In this redox system, the reduction of GSSG to GSH is catalyzed by the glutathione reductase. Equilibrium is sharply displaced in favor of the reduced glutathione and NADPH is required for cofactor.

In animal cells, glutathione has numerous key positions in internal biochemical processes, the effect of antioxidants probably being very important. Moreover, it plays an enormous role in the metabolism of cysteine-containing proteins and is involved in the deactivation of toxic, electrophilic agents during enzyme transports catalyzed by sulfur compounds.

In the metabolism, GSH assumes the task of a sulfhydryl buffer that, among other things, is to obtain the cysteine group of hemoglobin and other erythrocyte proteins in their reduced form. Tests demonstrated that reduced glutathione is indispensable for the natural structure of the erythrocytes because even a slightly lower level of GSH demonstrates a higher affinity of the blood corpuscles for hemolysis than is normally the case. Likewise important is the glutathione redox cycle for retaining normal mitochondrial function, whereby the GSH level here correlates to the activity of the carnitine acylcarnitine translocase, which thereby becomes an indicator for glutathione presence in the cells.

Glutathione possesses an important detoxification function during the production of by-products, such as hydrogen peroxides and natural peroxides, that is inevitable in aerobic life. Glutathione is involved in a specific scavenger system of the cells that is meant to counteract the oxygen radicals that provoke numerous changes. Thus for instance hydrogen peroxide and lipid peroxide are metabolized in the glutathione cycle in a reaction, catalyzed by glutathione peroxidase, with reduced glutathione while forming water and oxygen, which occurs in a large number of cells. The oxidized dimer of glutathione (GSSG) thus formed is then subsequently reduced to GSH again in the subsequent redox cycle.

The supporting effect of reduced glutathione and glutathione peroxidase in intracellular protection against damage by these reactive species was verified in numerous studies.

There can be severe pathophysiological consequences if too great a number of oxidants exceed the capacity of the glutathione metabolism, this resulting then in oxidative stress. The oxidants that are not detoxified can then attack structure proteins, enzymes, membrane lipids, and nucleic acids, and thus severely limit cell function.

Mitochondrial or glycolytic paths can lead to inhibition of ATP synthesis due to peroxide that has not been detoxified. Intracellular accumulation of GSSG, which in excess can itself lead to damage (reactions with free sulfhydryl groups of proteins), is sharply reduced using the function of ATP-dependent, carrier-related mechanisms.

In this case, the importance of the glutathione as protector recedes to a designed protective mechanism for the cell, which mechanism, with the use of glutathione and other reduction equivalents, prevents peroxide formations from occurring (on fatty acid chains). Like the cells of other organs, the myocytes are also naturally equipped with such an antioxidative enzyme system that contains superoxide dismutase (SOD) and catalase in addition to the glutathione redox system in order to protect itself from damage due to reactive compounds. Just the ability of glutathione to use hydrogen atoms from its thiol group as electron donors, and thus to bond and therefore deactivate most carbon-, oxygen-, or nitrate-laden radicals, creates efficacy as antioxidant.

Since glutathione has proved to be an important antioxidative substance in the heart and thus a protector, there are numerous scientific studies on the problem of the potential therapeutic usefulness of exogenous glutathione supply during cardiac infarct.

Furthermore, the usefulness of an external supply of glutathione was examined. In this case, first the myocardial glutathione in pre-treated animals ("Yorkshire pigs") was exhausted using a potent glutathione synthesis inhibitor in order then to be able to determine the extent of the damage after oxidative stress using untreated animals. A positive effect could be obtained using intravenous glutathione administration because with this external glutathione supply the myocardial glutathione content increased during ischemia and the reperfusion-induced damage or the extent of the myocardial infarct could be reduced. Various other work on isolated perfused heart models also indicated that enriching the perfusate with GSH clearly results in better recovery of ventricle function after ischemia and reperfusion. However, improved function is based less on an increase in the intracellular GSH level (GSH cannot be effectively transported into the cells) than on yet unexplained effects of the extracellular glutathione. After trials on a model of hypoxically damaged renal tubuli it was concluded that the cytoprotective effect of the exogenous glutathione can probably be traced to glycine, which occurs due to breakdown from GSH.

Glycine should also be mentioned; it forms in the glutathione-exhausted heart, presumably after the breakdown of reduced myocytes. Glycine's involvement in the detoxification of acyl CoA, an amphipathic molecule with limiting surface active properties and that accumulates particularly during myocardial ischemia, is not insignificant. Thus, in addition to the "switching function" of glutathione with respect to the inventive protonation of the photosensitizer, there is also a protective effect against damage due to the effect of the singlet oxygen on the local tissue.

2. Ascorbic Acid

Ascorbic acid possesses the following structures:

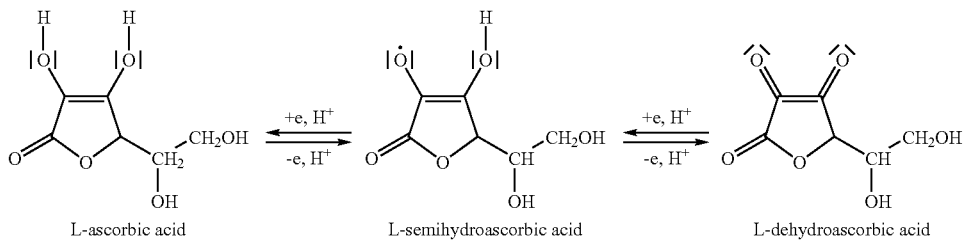

L-ascorbic acid      L-semihydroascorbic acid      L-dehydroascorbic acid

Ascorbic Acid as Proton Donor and Acceptor

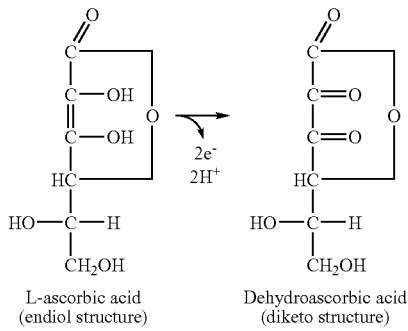

L-ascorbic acid (endiol structure)    Dehydroascorbic acid (diketo structure)

Structurally, ascorbic acid is a six-member carbon ketol actone related to glucose and other hexoses and is a water-soluble vitamin. In the body, it is reversibly oxidized to dehydroascorbic acid; it thus acts in the framework of a redox equilibrium as an electron donor and electron acceptor, which is also the basis for its main biological action. The significant redox processes occur between L-ascorbic acid (acts as 1-electron donor) and the radical L-semihydroascorbic acid.

In addition to numerous other tasks that ascorbic acid must fulfill in the metabolism, in this case its significance as an endogenous "scavenger" is of primary interest for us. This function as radical scavenger proceeds from specific scavenger systems with which the cells are equipped in order to protect themselves from oxygen radicals and other toxic oxygen metabolites that very clearly can lead to reversible and irreversible tissue damage, including damage to the myocardium. The free radicals can cause different types of damage, whereby peroxidation of membrane phospholipids and oxidation of sulfhydryl compounds are certainly the most significant. While in the framework of phospholipid peroxidation it is possible for various radical species to occur, such as lipid radicals, lipid alkoxyl radicals, lipid peroxides, and lipid hydroperoxides, in the case of oxidation of sulfhydryl compounds, essential membrane transport proteins and enzymes are inactivated, which itself leads to accumulation of certain electrolytes and thus to cell damage. With the assistance of the antioxidants that are bound into the endogenous protective systems (vitamin E and alpha-tocopherol, in addition to ascorbic acid), the cells attempt to control or terminate the continuing chain reactions that were initiated by explosion-like radical production.

Ascorbic acid is among the most highly reducing agents in the biological milieu.

The photodynamic effect can be controlled using protonation of the photosensitizer and control of the radical chain reaction.

3. Hydroquinone>Quinone

Quinones act with redox reactions in mitochondria (respiratory chain) and chloroplasts (photosythesis). A differentiation is made between ubiquinones and plastoquinones, which are characterized by different side chain groups on the quinone ring. As "coenzyme Q", an ubiquinone assumes a key position as primary electron acceptor in the photosystem II of the photosynthesis.

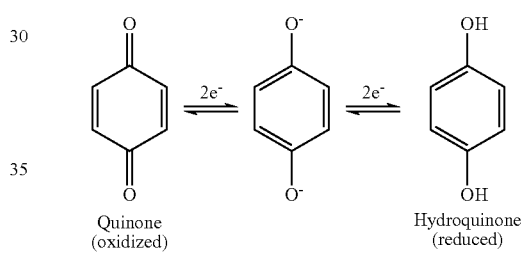

Quinone (oxidized)      Hydroquinone (reduced)

Hydroquinone, abbreviated $H_2Q$, can also be used for reducing agent or proton donor as for example also in photographic development.

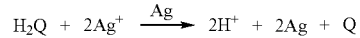

$$H_2Q + 2Ag^+ \xrightarrow{Ag} 2H^+ + 2Ag + Q$$

4. Alcohols and Aldehydes

Single or multivalent alcohols that are dehydrated to aldehydes can also act as proton donors. E.g. propanol or glycerin.

2.5 0.05 to 3% $Na_2S_2O_4$ Solution as Reducing Agent

6. Enzymatic Control:

Protonation and deprotonation of the photosensitizer can also be intensified and controlled using suitable enzymes such as for instance using xanthin dehydrogenase. Xanthin dehydrogenase is an enzyme with relatively low substrate specificity. It transfers hydrogen e.g. from formaldehyde or acetaldehyde to a suitable acceptor. This is possible for instance with the aforesaid methylene blue. The enzyme xanthin dehydrogenase can also be inhibited using urethane.

A similar reaction can be attained using the succinate dehydrogenase enzyme system, which catalyzes the succinate>fumarate step—a reaction that occurs in the citrate cycle. It can be competitively inhibited using a number of substances that are similar to the succinate.

The most well known and most common hydrogen acceptor is the nicotinamide adenine dinucleotide (NAD):

$$NAD^+ + 2e^- + 2H^+ <\,> NADH + H^+$$

or e.g.

$$NAD^+ + R\text{---}CHOH\text{---}R^1 <\,> NADH + H^+ + R\text{---}CO\text{---}R^1$$

One of the protons is bonded by NAD+ directly to the nicotinamide ring; the other remains in solution.

NAD+ is a coenzyme—it never acts alone, but rather only after bonding to a protein. NAD+-bonding proteins (enzymes) belong to the dehydrogenase class. All of them catalyze the same chemical reaction (see above), but they are different from one another in terms of their substrate specificity. Thus among many others there are alcohol dehydrogenase, lactate dehydrogenase, malate dehydrogenase, glycerin aldehydphosphate dehydrogenase, etc.

7. Intensification of the Singlet Oxygen Effect by Changing the Hydrogen/Deuterium Ratio The singlet oxygen that occurs during irradiation is also rapidly eliminated by the hydrogen atoms that are present in water. In a natural environment, the chemically equivalent isotope deuterium is very rare. By replacing a portion of the hydrogen atoms with the chemically equivalent deuterium, this elimination is significantly reduced and thus the antibacterial effect is intensified because the nanoenvironment of the bonded excited photosensitizer molecules and the singlet oxygen released by them is a deuterium environment rather than a hydrogen environment. A longer lifetime for the singlet oxygen means more reactivity against bacteria membrane molecules. This can be attained by replacing hydrogen with deuterium in the range of 0 to 100%.

One special embodiment of the invention is a rinse solution with which photodynamic control is further optimized. In the following, the actions are described for both the preparation described in the foregoing and for the rinse solution.

Photochemical inactivation of microorganisms involves a complex series of chemical reactions. In principle there are three basic reactions:
  Staining relevant microorganisms with a photochemically active dye
  Activating the dye with light of a suitable wavelength and energy density
  The sequence of the required inactivation reactions (membrane oxidation using radicals/singlet oxygen)
Thus two steps are critical for the clinical process:
  Staining with the photosensitizing dye
  Irradiating the target area Dyes for histological staining are composed of two essential components:

1. Chromophore group (dye carrier),
e.g. azo-, benzene compounds.

A chromophore group does not make a chemical into a dye, although it can appear colored to the eye.

A second component, called an auxochrome (color aid), is required for this.

2. Auxochrome groups (dye aids),
are either acid groups, e.g.
R—O(-) hydroxyl-,
R—COO(-) carboxyl-,
R—NO2(-) nitro-groups,
or basic groups e.g.
R—NH3(+) groups.

The type of auxochrome determines the classification as acid or basic dye. They are generally present in the form of the associated salts.

The theory of staining (Harms) states that positively charged, basic dyes accumulate on acid cell and tissue components, which then indicate the effect of basophilia. Conversely, negatively charged, acid dyes bond to positively charged, that is, acidophilic, components in cells and tissues.

| Tissue | Dye |
| --- | --- |
| Negatively charged (−) (acid) components e.g. nucleic acids, mucus "basophilia" | (+) Positively charged (basic) dyes e.g. methylene blue, methylene green |
| Positively charged (+) (basic) components e.g. eosinophilic granula "acidophilia" | (−) Negatively charged (acid) dyes e.g. eosin |

Building on the work of Robert Koch, Paul Ehrlich described the use of phenotiazine dyes for making visible bacteria in his publication "Über das Methylenblau und seine klinisch-bakterioskopische Verwertung" [On Methylene Blue and its Clinical/Bacterioscopic Use], Zeitschrift für klinische Medizin [Journal of Clinical Medicine], 1881; 2; 710-3. Dye solutions comprise dissolved dye molecules that react more or less specifically to membranes. Bacteria can be stained with methylene blue and detected in so-called simple staining.

The cellular membranes of microorganisms and cells are highly specific structures. Interaction with the environment is determined by local concentrations and charge conditions. Contact with the membrane is required for a molecule, for instance of a dye, to react.

This staining of bacteria occurs in aqueous solutions of 0.1% to 1% and as a rule these have a pH of 3-4. The staining molecule portion, the dye cation, is deposited on the wall of the bacteria using its positive surface charge, whereby these dyes are also called vital dyes.

The dye reaction also depends in part on the pH of the specimen to be stained. An acid pH intensifies the reaction with the basic methylene blue (blue dye).

During photochemical germ activation, the accumulated dye cation is now used as a "photochemical machine" that absorbs the laser light and is converted to chemical energy, which is used for the production of singlet oxygen.

The irradiation is influenced primarily by the selection of a suitable wavelength, which should approach the absorption maximum for the dye, and the selection of adequate surface and energy densities, but primarily also by the uniform spatial distribution of the light. This is especially critical when complex structures with different optical properties have to be treated, such as teeth, bones, and mucosa in a single area.

Surprisingly, it was demonstrated that the effect of the photochemical inactivation of microorganisms can be improved substantially when a third step is introduced:

In accordance with the invention, the therapy area is prepared, after the staining and prior to the irradiation, by rinsing out the dye solution with a suitable rinse solution.

In clinical trials, patients with demonstrated bacterial infections in periodontal pockets had these rinsed with 0.1% solution of methylene blue and thus the bacteria and plaque present there was stained.

Finally, the pockets were irradiated with a laser via optics and then all of the pockets were rinsed thoroughly with an aqueous solution in order to remove as much residual dye as possible.

After rinsing with the rinse solution, a specimen was again taken from the pockets in order to determine the remaining bacterial colonies.

During an expanded series of trials, after careful rinsing to remove the residual dye the pockets were re-irradiated with laser and optics for one minute. The resulting bacterial counts for two patients are shown in Table 1.

TABLE 1

Comparison of bacterial counts for two patients prior to treatment, after treatment, and after re-irradiation after rinsing.

| Type of bacteria | Patient 1 Prior to treatment | Patient 1 After irradiation 1 | Patient 1 After irradiation 2 | Patient 2 Prior to treatment | Patient 2 After irradiation 1 | Patient 2 After irradiation 2 |
|---|---|---|---|---|---|---|
| *Actinobacillus actinomycetemcom.* | $<1.0 \times 10^2$ | $<1.0 \times 10^2$ | $<1.0 \times 10^2$ | $<2.7 \times 10^3$ | $<4.5 \times 10^2$ | $<1.0 \times 10^2$ |
| *Porphyromonas gingivalis* | $<2.5 \times 10^2$ | $<1.5 \times 10^2$ | $<1.5 \times 10^2$ | $<4.6 \times 10^4$ | $<1.3 \times 10^3$ | $<2.9 \times 10^2$ |
| *Tannerella fosythensis* | $<1.7 \times 10^5$ | $<5.7 \times 10^3$ | $<2.5 \times 10^2$ | $<6.3 \times 10^5$ | $<5.3 \times 10^3$ | $<2.5 \times 10^2$ |
| *Treponema denticola* | $<6.6 \times 10^4$ | $<6.6 \times 10^3$ | $<2.5 \times 10^2$ | $<4.7 \times 10^5$ | $<4.1 \times 10^3$ | $<2.5 \times 10^2$ |
| *Fusobacterium nucleatum* ssp. | $<2.6 \times 10^5$ | $<4.4 \times 10^3$ | $<2.8 \times 10^2$ | $<3.1 \times 10^5$ | $<6.2 \times 10^3$ | $<2.5 \times 10^2$ |
| *Prevotella intermedia* | $<1.0 \times 10^2$ | $<1.0 \times 10^2$ | $<1.0 \times 10^2$ | $<1.0 \times 10^2$ | $<1.0 \times 10^2$ | $<1.0 \times 10^2$ |
| Total | $<4.2 \times 10^8$ | $<2.3 \times 10^8$ | $<2.1 \times 10^7$ | $<4.2 \times 10^8$ | $<4.8 \times 10^7$ | $<1.4 \times 10^7$ |

Prior to treatment = Specimen removed prior to dye reaction
After irradiation 1 = Specimen removed after irradation with dye solution
After irradiation 2 = Specimen removed after irradiation after rinsing out dye It can be seen that the re-irradation after rinsing out dye solution surprisingly intensifies the photochemical bactericidal effect.

It was not possible to attain a similar effect when the specimen was taken immediately after rinsing the dye out without re-irradiation. This effect was thus not attained by "rinsing out" the bacteria.

Nor could a comparable effect be attained by irradiating twice after rinsing. This effect is not based on increasing the irradiation dosage, either.

Thus the effect of the irradiation was surprisingly clearly improved with rinsing the therapy area with the rinse solution prior to irradiation.

A study of significant parameters for the rinse solution demonstrated that the following chemical and optical parameters of the therapy area were changed:
pH
Ion concentration
Optical transparency
Protein concentration With the rinsing after staining the microorganisms prior to irradiation, the effect of the light can be improved with deliberate adjustment of optical and chemical parameters and the most undisturbed sequence for the photochemical reaction chain can be assured.

The rinse solution should possessed [sic] at least one of the following properties:
The pH of the therapy area is changed from the range of 3-4, which is the range most favorable for staining microorganisms, to the range 7 to 9, which is favorable for singlet oxygen formation. Singlet oxygen formation and thus the oxidative attack on the membrane of microorganisms is up to 5 times higher in solutions with a pH of 7-9 than in a range of pH 3-4.
The ion concentration is changed and the buffer systems weakened (for instance from blood and saliva). Singlet oxygen formation increases with unbuffered or weakly buffered solutions from pH 5-6 by twice the amount if one compares highly buffered solutions having the same pH.
The extinction of the liquid in the therapy area is reduced. Depending on the concentration of the dye solution, a coating of 200 μm for a 1% methylene blue solution leads to 95% absorption of the light! On the other hand, dye molecules in the sense of the therapy are active if they are directly electrostatically bonded to the membrane of microorganisms. The lifetime of the deciding reactants for the photochemical reactions are:

Excited photosensitizer molecule=1×10-9 sec
Singlet oxygen=1×10-4 to 10-7

Thus the mean free path length for the reactive singlet oxygen molecules is approx. 0.2 nm. Therefore their reaction options are also limited to this radius around the molecule. The dye molecules remaining in free solution are thus not useful in the sense of the therapy, but rather even impede the therapeutic effect by increasing the extinction.

It has a hemostatic effect and/or reduces in general the concentration of plasma proteins, because these can also act as competing reaction partners for singlet oxygen and formed radicals.

Thus rinse solutions with an aqueous or non-aqueous basis are provided that have at least one of the following properties:
have a pH of 7-9,
do not contain concentrations of compounds that could act as buffer systems (e.g., phosphates, citrates, carbonates),
do not increase the extinction of the laser light used,
effectively rinse out the dye solution,
have a hemostatic effect.

In accordance with the invention, the preparation that contains dye or is a dye is initially applied in a high concentration to the area to undergo therapy and then rinsing is performed with the rinse solution, in particular water and/or with a basic pH that is as high as possible. Then the irradiation is performed by means of the light from the irradiation device, optimized cell damage occurring in a preferred manner. It has proved particularly effective to initially apply the preparation in a high concentration to the area to undergo therapy and then to rinse with the rinse solution, in particular water and/or with an oxygen partial pressure that is as high as possible, and finally to perform the irradiation by means of the light from the aforesaid light source, optimized cell damage preferably occurring. Moreover, it has proved particularly useful that after applying the preparation in a high concentration to the area to undergo therapy and prior to irradiation by means of the light from the light source, a reduction in the quantity of the preparation is performed, specifically in particular by wiping and/or blotting and/or suctioning and/or blowing off.

Application of the light-activatable substance is begun slowly and is applied by means of syringe so that it covers the surface of the infected tissue area. The quantity must be selected such that the surfaces of the infected areas are wetted with the thinnest possible coating of the light-activatable substance. It should be ensured that the niches and pockets in the tissue are completely wetted. Likewise, the air blower should be used if there is complex morphology. The exposure time for the light-activatable substance is at least 60 sec. After rinsing for at least 3 sec with simultaneous suctioning of excess solution (deposits of dye must be removed!), irradiate with the irradiation device. The correct dosage of energy, the irradiation, is significant in terms of the bacteria-reducing effect and is thus significant for the treatment results.

After the exposure time for the preparation or photosensitizer (PS), which is at least 60 sec., has elapsed, in accordance with the invention the excess PS is rinsed out and the rinse solution is simultaneously suctioned. Thus PS and exudate are removed and only the remaining residue is available for oral ingestion.

Table of dilutions after rinsing and suctioning of PS

| Rinse solution in ml | Dilution | MB Content in % | Molar | MB content in mg/ml | mg substance in 0.5 ml |
|---|---|---|---|---|---|
| 0 | Starting solution | 1 | 0.031 | 10 | 5 |
| 5 | 1.10 | 0.01 | 0.003 | 1 | 0.5 |
| 50 | 1:100 | 0.001 | 0.0003 | 0.01 | 0.05 |

As can be seen from the table above, given rinsing, dilution, and suctioning of the PS, 0.5 mg substance remains by a factor of 10, and 0.05 mg still remain given dilution by a factor of 100. For 100× dilution (rinsing with water) assuming that the total remaining quantity is ingested orally and resorbed, in an adult with an average assumed body weight of 65 kg this would be the equivalent of 0.0008 mg per kg body weight or 0.08 micrograms per kg body weight. In a child with an assumed weight of 20 kg, this would be 0.0025 milligrams per kg body weight, or 2.5 micrograms per kg body weight.

A daily maximum dosage up to 200 mg is provided for the 1% solution for injection used as antidote. This means a kg dosage per day of approx. 3 mg for an adult and 10 mg/day/kg for a child.

A maximum of 5 mg MB are dissolved in 0.5 ml 1% solution. Even if the patient swallows all of it, the kg dosage per day is only approx. 80 µg and is only 250 µg for a child. This is the equivalent of only approx. 2.5% of the dosage recommended for detoxification, without taking into account the therapeutically recommended dilution prior to irradiation.

Another significant factor that relates to rinsing out the preparation or the photosensitizer (PS) prior to irradiation is the high absorption of the preparation or the photosensitizer (PS) in the range of the wavelength of the light applied.

Measurements demonstrate that a liquid film of the preparation or of the photosensitizer of 100 µm standing on the tissue reduces the effective energy density by 97%. In accordance with the Beer/Lampert Law, the light is further weakened when the coating thickness is doubled. Thus therapeutically effective irradiation is not possible when there is excess preparation or photosensitizer.

Due to rinsing with the rinse solution, in particular water, having the lowest possible ion concentration, bacteria and/or cell membranes are jeopardized due to the osmotic pressure gradients created therewith. It should be noted that for instance a physiological table salt solution would not be favorable due to the relatively high ion concentration. The pH value for the rinse solution is preferably more basic. It preferably has a pH of 7 to 9. The oxygen partial pressure is preferably high. In the framework of the invention, the rinse solution, in particular prepared tap water, has oxygen partial pressure in the range of 4 to 6 mg/l for rinsing. The rinse solution is usefully enriched with molecular oxygen up to 14 mg/l. Moreover, in accordance with the invention, peroxide enrichment has proved useful, specifically preferably as 0.5% to 3% hydrogen peroxide solution.

Due to prior rinsing with the rinse solution having a low ion concentration, optimum cell damage is accomplished during irradiation by means of the laser light. The preparation and combination with the rinse solution inventively results in a deliberate change in the pH in the work area in three steps:

Staining in the acid range, in particular at a pH between 3 and 5

Adjusting or turning off more in the acid range, by means of the rinse solution, in particular ascorbic acid Irradiating in the neutral to slightly basic range, in particular at a pH between 7 and 9

The invention claimed is:

1. A kit of compositions for photodynamic control of microorganisms present in a selected treatment area, the kit comprising:
a liquid or paste preparation for photodynamic control of microorganisms comprising an aqueous solution including a photosensitizer comprising a dye capable of staining microorganisms present in the selected treatment area that, when irradiated with laser light, induces formation of singlet oxygen, the microorganisms being capable of being marked with the dye, the dye being present in a concentration of 0.1% to 1.0%;
an active substance for modulating the oxidative effect of formed singlet oxygen by chemical interaction with the dye or its nanoenvironment;
an ion-containing rinse solution capable of rinsing out the photosensitizer after staining microorganisms present in the selected area in need of treatment and capable of adjusting the pH value in the selected treatment area to 7 to 9, the rinsing out of the photosensitizer with the rinse solution occurring before irradiating the selected treatment area with laser light from a laser light source;
whereby upon treatment of the selected area in need of treatment, optimized cell damage to the microorganisms is effected.

2. The kit of claim 1 wherein the rinse solution has a water base.

3. The kit of claim 1 wherein the rinse solution does not increase the extinction of the laser light when the dye is irradiated with laser light.

4. The kit of claim 1 wherein the rinse solution has an oxygen concentration of 4 to 6 mg/l.

5. The kit of claim 1 wherein the rinse solution comprises molecular oxygen at up to 14 mg/l.

6. The kit of claim 1 wherein the rinse solution comprises a peroxide.

7. The kit of claim 6, wherein the rinse solution comprises 0.5 to 3 wt-% hydrogen peroxide.

8. The kit of claim 1, wherein the dye is reversibly activatable with respect to its light absorption.

9. The kit of claim 8 wherein the dye can be switched between active and inactive forms via protonation using chemical proton donors.

10. The kit of claim 1 wherein a radical chain reaction is controlled by protonation of the photosensitizer by a proton donor.

11. The kit of claim 1 wherein the active substance of the preparation is selected from the group consisting of glutathione, ascorbic acid, hydroquinone, quinine, an alcohol, an aldehyde, an enzyme, hydrogen, and deuterium.

12. A method of photodynamic treatment for control of microorganisms comprising the steps of:
- applying a liquid or paste preparation for photodynamic control of microorganisms to a selected treatment area, the liquid or paste preparation comprising:
- an aqueous solution of a photosensitizer comprising a dye capable of staining microorganisms in the selected treatment area that, when irradiated with light, induces formation of singlet oxygen, the microorganisms being capable of being marked with the dye, the dye being present in the aqueous solution in a concentration of between 0.1% to 1.0%, whereby, upon application of the liquid or paste preparation, microorganisms in the selected treatment area are stained, and
- an active substance for modulating the oxidative effect of the singlet oxygen by chemical interaction with the dye or its nanoenvironment;
- prior to an irradiation step, rinsing the selected treatment area for at least 3 seconds with an ion-containing rinse solution for rinsing out the photosensitizer after staining of the microorganisms present in the selected treatment area, whereby the rinse solution adjusts the pH value in the selected treatment area to a range of 7 to 9; and
- irradiating the selected treatment area with laser light from a laser light source for at least 60 seconds,
- whereby upon treatment of the selected treatment area, optimized cell damage to the microorganisms is effected.

13. The method of claim 12 wherein the rinse solution comprises water.

14. The method of claim 12 wherein the rinse solution functions as a weak pH buffer in the selected treatment area.

15. The method of claim 12 wherein the rinse solution reduces the ion concentration or the concentration of plasma proteins in the selected treatment area.

16. The method of claim 12 wherein, prior to the irradiation, the quantity of dye in the selected treatment area is reduced by wiping, blotting, suctioning, or blowing off.

17. The method of claim 12 wherein the active substance of the preparation is ascorbic acid.

18. The method of claim 12 wherein the active substance of the preparation is selected from the group consisting of glutathione, ascorbic acid, hydroquinone, quinine, an alcohol, an aldehyde, an enzyme, hydrogen, and deuterium.

19. The method of claim 12 wherein the preparation is applied to the selected treatment area with a syringe.

20. A method of photodynamic treatment for control of microorganisms comprising the steps of:
- applying to a selected treatment area a liquid or paste preparation for photodynamic control of microorganisms comprising:
- an aqueous solution of a photosensitizer comprising a dye capable of staining microorganisms in the selected treatment area that, when irradiated with light, induces formation of singlet oxygen, the microorganisms being capable of being marked with the dye, the dye being present in the aqueous solution in a concentration of between 0.1% to 1.0%, the application of the liquid or paste preparation being performed at a pH value in the range of 3 to 5 in the selected treatment area, whereby upon application of the liquid or paste preparation, microorganisms in the selected treatment area are stained, and
- an active substance for modulating the oxidative effect of the singlet oxygen by chemical interaction with the dye or its nanoenvironment;
- prior to an irradiation step, rinsing the selected treatment area for at least 3 seconds with an ion-containing rinse solution for rinsing out the photosensitizer after staining of the microorganisms, whereby the rinse solution adjusts the pH value in the selected treatment area to a range of 7 to 9; and
- irradiating the selected treatment area with laser light from a laser light source for at least 60 seconds,
- whereby upon treatment of the selected treatment area, optimized cell damage to the microorganisms is effected.

21. The method of claim 20 wherein the active substance of the preparation is ascorbic acid.

* * * * *